United States Patent
Ichioka et al.

(10) Patent No.: US 11,111,211 B2
(45) Date of Patent: Sep. 7, 2021

(54) METHOD OF DISTILLING DIMETHYL SULFOXIDE AND MULTISTAGE DISTILLATION TOWER

(71) Applicant: Toray Fine Chemicals Co., Ltd., Tokyo (JP)

(72) Inventors: Ryoji Ichioka, Tokai (JP); Haruo Murano, Ichihara (JP)

(73) Assignee: Toray Fine Chemicals Co., Ltd., Tokyo (JP)

( * ) Notice: Subject to any disclaimer, the term of this patent is extended or adjusted under 35 U.S.C. 154(b) by 229 days.

(21) Appl. No.: 16/463,680

(22) PCT Filed: Jan. 5, 2018

(86) PCT No.: PCT/JP2018/000060
§ 371 (c)(1),
(2) Date: May 23, 2019

(87) PCT Pub. No.: WO2018/189969
PCT Pub. Date: Oct. 18, 2018

(65) Prior Publication Data
US 2020/0308108 A1    Oct. 1, 2020

(30) Foreign Application Priority Data
Apr. 12, 2017 (JP) ............................. JP2017-078881

(51) Int. Cl.
*B01D 3/14* (2006.01)
*C07C 315/06* (2006.01)
(Continued)

(52) U.S. Cl.
CPC ............ *C07C 315/06* (2013.01); *B01D 3/146* (2013.01); *B01D 3/32* (2013.01); *B01D 3/34* (2013.01);
(Continued)

(58) Field of Classification Search
CPC ...... C07C 315/06; C07C 317/04; B01D 3/146; B01D 3/32; B01D 3/34; B01D 3/4277; B01D 5/006
See application file for complete search history.

(56) References Cited

U.S. PATENT DOCUMENTS 3,376,203 A * 4/1968 Lackey ................. A61K 31/10
568/27
4,964,957 A * 10/1990 Shaw ....................... B01D 3/34
203/29
(Continued)

FOREIGN PATENT DOCUMENTS

CN       204342710       5/2015
JP       38-20721        10/1963
(Continued)

OTHER PUBLICATIONS

CN204342710U Machine Translation from ESPACENET obtained Mar. 4, 2021. (Year: 2021).*
(Continued)

*Primary Examiner* — Jonathan Miller
(74) *Attorney, Agent, or Firm* — DLA Piper LLP (US)

(57) ABSTRACT

A method of distilling a liquid containing dimethyl sulfoxide using a distillation system, including mixing sodium carbonate with a liquid containing dimethyl sulfoxide at a bottom of the distillation system such that sodium carbonate accounts for 0.005% to 25% by weight relative to 100% by weight of the liquid containing dimethyl sulfoxide and sodium carbonate in total at the bottom of the distillation system and heating the bottom; and obtaining a distillate containing dimethyl sulfoxide at a position lower than a position at which the liquid containing dimethyl sulfoxide is introduced and higher than a position of the heating portion.

13 Claims, 8 Drawing Sheets

(51) Int. Cl.
- *B01D 3/32* (2006.01)
- *B01D 3/34* (2006.01)
- *B01D 3/42* (2006.01)
- *B01D 5/00* (2006.01)
- *C07C 317/04* (2006.01)

(52) U.S. Cl.
CPC ........... *B01D 3/4277* (2013.01); *B01D 5/006* (2013.01); *C07C 317/04* (2013.01)

(56) References Cited

U.S. PATENT DOCUMENTS

| | | | |
|---|---|---|---|
| 10,435,360 B2* | 10/2019 | Murano | ............... C07C 315/06 |
| 2018/0354899 A1* | 12/2018 | Murano | ............... C07C 315/06 |

FOREIGN PATENT DOCUMENTS

| | | |
|---|---|---|
| JP | 43-3765 | 2/1968 |
| JP | 60-1302 | 1/1985 |
| JP | 2015-145359 A | 8/2015 |
| WO | 2017/064910 A1 | 4/2017 |

OTHER PUBLICATIONS

Santosusso, M. Thomas, et al., "Acid Catalysis in Dimethyl Sulfoxide Reactions. A Generally Unrecognized Factor", *The Journal of Organic Chemistry*, 41(16):2764-2768. 1976. https://www.researchgate.net/publication/231598576_Chemistry_of_epoxides_XXXII_Acid_catalysis_in_dimethyl_sulfoxide_reactions_A_generally_unrecognized_factor Abstract Only.

* cited by examiner

METHOD OF DISTILLING DIMETHYL SULFOXIDE AND MULTISTAGE DISTILLATION TOWER

TECHNICAL FIELD

This disclosure relates to a method of distilling dimethyl sulfoxide (DMSO). In particular, the disclosure relates to a method of distilling a liquid containing dimethyl sulfoxide using a distillation system including a multistage distillation tower to distill dimethyl sulfoxide.

BACKGROUND

Dimethyl sulfoxide has been industrially widely used as a solvent for removal of electronic materials, washing solvents, synthesis of medicines and pesticides, polymer polymerization, spinning of fibers of such polymers and the like. Recovery of dimethyl sulfoxide components from a waste liquid after use and reuse of the components have been industrially widely carried out. A step of heat-distilling a waste liquid containing dimethyl sulfoxide to purify dimethyl sulfoxide is an essential step to recover and reuse dimethyl sulfoxide.

Meanwhile, dimethyl sulfoxide is thermally unstable. It is known that when dimethyl sulfoxide is boiled or distilled at atmospheric pressure, dimethyl sulfoxide is partially decomposed. When distillation purification is conducted over the course of production or recovery of dimethyl sulfoxide, thermal decomposition products are present as impurities. To prevent reduction of the performance of dimethyl sulfoxide as a solvent, vacuum distillation is usually conducted under high vacuum to reduce the boiling temperature.

In general, in vacuum distillation of dimethyl sulfoxide, as distillation operation pressure decreases, the volume and flow velocity of vapor moving up in a tower increases. It is therefore necessary to reduce the flow velocity of vapor to stabilize the operation. Reduction of the flow velocity of vapor requires reduction of the feed rate in a conventional distillation tower, which results in an increase in the dimethyl sulfoxide recovery cost. When a distillation tower is newly constructed, the tower diameter should be increased to reduce the flow velocity of vapor and, thus, the plant size of a recovery unit as a whole is increased, which causes an increase in the plant construction investment cost.

In addition, it is often that a continuous distillation unit, for which a large amount of energy is used for heating or cooling, decreases the amount of energy used by recovering and effectively using sensible heat or evaporative latent heat of an in-process liquid or vapor. In particular, it becomes easier to effectively use vapor as a heating medium at a higher vapor temperature for the use of evaporative latent heat in vapor condensation. Thus, the vapor can be widely used to heat fluid in a different process or generate medium-pressure/high-pressure steam in many systems. However, as the vapor temperature is low in vacuum distillation of dimethyl sulfoxide under high vacuum, heat cannot be sufficiently effectively used and is often partially released.

Further, there is a problem in vacuum distillation of dimethyl sulfoxide when a waste liquid contains large amounts of low-boiling point components having lower boiling points than that of dimethyl sulfoxide such as water, as the degree of vacuum increases, the vapor condensing temperature decreases during distillating separation of the low-boiling point components. As a result of reduction of the vapor condensing temperature, it is required to use a low-temperature refrigerant such as chilled water or brine which is expensive in terms of the unit cost for a refrigerant of a condenser, which results in high distillation cost and increasing load on a low-temperature refrigerant production system.

To conduct economical efficient distillating purification of dimethyl sulfoxide, there have been a lot of researches decomposition inhibitors of dimethyl sulfoxide to increase the pressure or temperature upon distillation of dimethyl sulfoxide.

Methods of distillation purification of dimethyl sulfoxide by distillation with the addition of bases are known. For example, a method comprising adding an alkali metal hydroxide such as lithium hydroxide, sodium hydroxide, potassium hydroxide, rubidium hydroxide, or cesium hydroxide (see Japanese Examined Patent Publication (Kokoku) No. 43-3765 and Japanese Examined Patent Publication (Kokoku) No. 38-20721) and a method comprising introducing granular sodium hydroxide and potassium hydroxide to swell sodium hydroxide and potassium hydroxide and then removing the sodium hydroxide and potassium hydroxide (see Japanese Examined Patent Publication (Kokoku) No. 60-1302) are known.

However, it has been reported that the method comprising adding alkali metal hydroxide to dimethyl sulfoxide is limited to a method in which granular sodium hydroxide and potassium hydroxide in amounts accounting for 0.003% to 0.5% are introduced because, when sodium hydroxide and potassium hydroxide in amounts accounting for more than 0.5% are added, the amounts of decomposition products increase. It also has been reported that the amounts of sodium hydroxide and potassium hydroxide to be added are limited to an amount accounting for 0.5% in a method comprising adding sodium hydroxide to dimethyl sulfoxide to swell sodium hydroxide and then removing the sodium hydroxide and potassium hydroxide because when sodium hydroxide and potassium hydroxide in amounts accounting for more than 0.5% are added, the amounts of decomposition products increase.

Japanese Examined Patent Publication (Kokoku) No. 43-3765, Japanese Examined Patent Publication (Kokoku) No. 38-20721 and Japanese Examined Patent Publication (Kokoku) No. 38-20721 teach the conditions for adding alkali metal hydroxide based on the evaluation results of thermal decomposition of dimethyl sulfoxide by batch-type distillation. However, in batch-type distillation, the distillate amount during operation increases and the concentration of bases in a liquid remaining in a vessel increases. In continuous distillation, the concentration of bases in a tower bottom liquid becomes greater than that of in a distillation feed. As a result, in continuous distillation, bases are concentrated at a tower bottom that may cause thermal decomposition of dimethyl sulfoxide to proceed in the presence of highly concentrated bases at the tower bottom. Further, deposition of base crystals from highly concentrated bases causes scaling or crystal deposition on a reboiler heat-transfer surface, a tower tray, a packing bed, a liquid distributer, a liquid collector and the like. In particular, upon continuous distillation, deposition of base crystals in a distillation tower results in promoted thermal decomposition of dimethyl sulfoxide at a local site with a high base concentration because the concentration of slurry of the internal liquid is not equal at random sites in the tower. Therefore, in many continuous distillation methods, the dimethyl sulfoxide recovery rate should be decreased to suppress an increase in the base concentration to prevent thermal decomposition of dimethyl sulfoxide and, further, an apparatus such as a stirrer or a pump with a large flow rate for liquid circulation is installed to decrease the degree of base concentration at a tower bottom portion.

In distillation purification conducted over the course of production or recovery of dimethyl sulfoxide, distillation purification is carried out in the continuous distillation process by which a large amount of dimethyl sulfoxide can be produced or recovered to obtain high quality dimethyl sulfoxide at a high yield. In the continuous distillation process, it is usual to conduct distillation at temperatures and pressures that do not cause thermal decomposition of dimethyl sulfoxide in each tower when using at least two distillation towers which are a lightends tower for distillation separation of lightends (low-boiling point components) represented by water having lower boiling points than that of dimethyl sulfoxide and a heavyends tower for separating heavyends (high-boiling point components). However, to reduce the distillation system construction investment cost, it is desirable to combine distillation towers to decrease the number of towers to simplify the process in a compact manner.

It could therefore be helpful to provide a method of distilling dimethyl sulfoxide, whereby a large amount of dimethyl sulfoxide can be produced or recovered by a compact and simple process or a compact distillation system, thereby obtaining high quality dimethyl sulfoxide at a high yield.

It could also be helpful to provide a multistage distillation tower, whereby a large amount of dimethyl sulfoxide can be produced or recovered, thereby obtaining high quality dimethyl sulfoxide at a high yield.

SUMMARY

We thus provide:

A method of distilling a liquid containing dimethyl sulfoxide using a distillation equipment, comprising:

(1) mixing sodium carbonate with a liquid containing dimethyl sulfoxide at a bottom of the distillation equipment such that sodium carbonate accounts for 0.005% to 25% by weight relative to 100% by weight of the liquid containing dimethyl sulfoxide and sodium carbonate in total at the bottom of the distillation equipment and heating the bottom; and (2) obtaining a distillate containing dimethyl sulfoxide at a position lower than a position at which the liquid containing dimethyl sulfoxide is introduced and higher than a position of the heating portion.

A multistage distillation tower that distills a liquid containing dimethyl sulfoxide, which includes an equipment apparatus that adds sodium carbonate at the tower bottom of the distillation tower, and provided with an equipment capable of mixing sodium carbonate with a liquid containing dimethyl sulfoxide at the tower bottom of the distillation tower and heating the bottom portion, while controlling the concentration of sodium carbonate to 0.005% to 25% by weight relative to 100% by weight of the liquid containing dimethyl sulfoxide and sodium carbonate in total at the tower bottom of the distillation tower, wherein a side cut that allows a distillate containing dimethyl sulfoxide to flow out at a position lower than a position of a supply stage for supplying a liquid containing dimethyl sulfoxide and higher than a position of the heating portion.

According to the method of distilling dimethyl sulfoxide, compact equipment is achieved and, thus, the system construction investment cost is low. Further, as the temperatures of an in-process liquid and vapor in a distillation tower increase, it is possible to reduce the amount of energy used in the system as a whole by reusing energy through recovery of sensible heat and latent heat of the in-process liquid and vapor. This allows distillation purification of dimethyl sulfoxide at a low purification cost in an economical manner.

According to the method of distilling dimethyl sulfoxide, a large amount of dimethyl sulfoxide can be produced, and high quality dimethyl sulfoxide can be obtained at a high yield; a large amount of dimethyl sulfoxide can be recovered, and high quality dimethyl sulfoxide can be obtained at a high yield; a large amount of dimethyl sulfoxide can be produced, and high quality dimethyl sulfoxide can be obtained at a high yield by a compact system; a large amount of dimethyl sulfoxide can be recovered, and high quality dimethyl sulfoxide can be obtained at a high yield by a compact system.

According to the multistage distillation tower, as the temperatures of an in-process liquid and vapor in a distillation tower increase, it is possible to reduce the amount of energy used in the system as a whole by reusing energy through recovery of sensible heat and latent heat of the in-process liquid and vapor. This allows distillation purification of dimethyl sulfoxide at a low purification cost in an economical manner.

Dimethyl sulfoxide obtained by the method of distilling dimethyl sulfoxide contains fewer impurities and has high purity. Dimethyl sulfoxide obtained by the method of distilling dimethyl sulfoxide can be used as a liquid to remove photoresists as electronic materials, a liquid for to synthesis of medicines and pesticides, a liquid to remove washing lend molds or the like, a solvent used in a step of polymerization of polymers such as cellulose, polyimide, polysulfone, polyurethane, and polyacrylonitrile or spinning of fibers of such polymers, or a liquid for removing paints.

Dimethyl sulfoxide recovered or purified according to the multistage distillation tower contain fewer impurities and has high purity. Dimethyl sulfoxide according to the method of distilling dimethyl sulfoxide can be widely used as a solvent to remove or wash electronic materials, synthesis of medicines and pesticides, polymer polymerization, spinning of fibers of such polymers, and the like.

REFERENCE SIGNS LIST

1: Distillation tower
2: Stage (packing bed in the drawings)
3: Reboiler
4: Condenser
5: Pipe for feed a starting material
6: Pipe for transferring overhead vapor in a distillation tower to a condenser
7: Condenser vent pipe
8: Condensation liquid drip pipe
9: Condensation liquid drawing off pipe
10: Condensation liquid reflux pipe
11: Pipe for drawing off a dimethyl sulfoxide product via a side cut
12: Pipe for drawing off heavyends
13: Pipe for adding a degradation inhibitor (sodium carbonate)
14: Distillation tower in other distillation equipment
15: Stage (packing bed in the drawings) in other distillation equipment
16: Exhausted heat recovery condenser
17: Condenser in other distillation equipment
18: Pipe for supplying a feed material in other distillation equipment
19: Pipe for transferring overhead vapor in a distillation tower to a condenser in a different distillation system
20: Condenser vent pipe in other distillation equipment
21: Condensation liquid drip pipe in other distillation equipment
22: Condensation liquid discharge pipe in other distillation equipment
23: Condensation liquid reflux pipe in other distillation equipment
24: Circulation pipe for heating a tower bottom liquid in other distillation equipment
25: Pipe for discharging high-boiling point components in other distillation equipment

DETAILED DESCRIPTION

We provide a method of distilling a liquid containing dimethyl sulfoxide using distillation equipment.

A liquid containing dimethyl sulfoxide is, for example, a reaction solution containing dimethyl sulfoxide obtained in a step of synthesis via oxidation of dimethyl sulfide or the like, a waste liquid containing dimethyl sulfoxide used as a liquid to remove photoresists as electronic materials, a waste liquid containing dimethyl sulfoxide used as a liquid to remove/wash lens molds or the like, a waste liquid containing dimethyl sulfoxide used in a solvent for synthesis of medicines and pesticides, a waste liquid containing dimethyl sulfoxide used in a step of polymerization of polymers such as cellulose, polyimide, polysulfone, polyurethane, and polyacrylonitrile or spinning of fibers of such polymers, or a waste liquid containing dimethyl sulfoxide used as a liquid for removing paints.

When the concentration of dimethyl sulfoxide in a liquid containing dimethyl sulfoxide is excessively low, the cost of distillation of components other than dimethyl sulfoxide increases. Therefore, the concentration of dimethyl sulfoxide in a liquid containing dimethyl sulfoxide is preferably 10% by weight or more and more preferably 20% by weight or more.

The liquid containing dimethyl sulfoxide may contain water. The water content in the liquid containing dimethyl sulfoxide is usually 0.002% to 99.99%.

Sodium carbonate is mixed with a liquid containing dimethyl sulfoxide at a bottom of the distillation system such that sodium carbonate accounts for 0.005% to 25% by weight relative to 100% by weight of the liquid containing dimethyl sulfoxide and sodium carbonate in total at the bottom of the distillation equipment.

The bottom of the distillation equipment is a portion in which an in-process liquid to be evaporated when heated by a heater is retained at the highest temperature at the bottom of the distillation equipment.

Sodium carbonate may be either anhydrate or hydrate. A hydrate of sodium carbonate is preferably a monohydrate or decahydrate thereof, which is easily available.

Sodium carbonate is mixed with a liquid containing dimethyl sulfoxide at the bottom of the distillation equipment such that sodium carbonate accounts for 0.005% to 25% by weight relative to 100% by weight of the liquid containing dimethyl sulfoxide and sodium carbonate in total at the bottom of the distillation equipment. When the mixed amount of sodium carbonate accounts for less than 0.005% by weight, dimethyl sulfoxide is likely to be decomposed. In addition, when the mixed amount of sodium carbonate accounts for more than 25% by weight, the property of slurry at the bottom of the distillation equipment deteriorates, which causes crystal deposition at the bottom of the distillation system, scaling on the reboiler heat-transfer surface, or clogging upon discharge to a significant extent and results in difficulties in the operation and work. The mixed amount of sodium carbonate is preferably 0.08% by weight to 20% by weight, assuming that the total of the liquid containing dimethyl sulfoxide and sodium carbonate is 100% by weight.

Sodium carbonate can be added in the powder or solid form. It is also possible to mix sodium carbonate with an appropriate solvent such as water and add the mixture in the aqueous solution or slurry form at the bottom of the distillation equipment. Sodium carbonate adhering to the inside of the distillation equipment has a large solubility in water and thus, it can be easily washed using water, hot water, or water vapor. Sodium carbonate adhering to the inside of the distillation equipment may be recovered or reused.

It is preferable to directly add sodium carbonate at the bottom of the distillation equipment.

It is preferable to preliminarily add sodium carbonate to a liquid at the tower bottom provided with a reboiler in the distillation equipment and then start the operation to not cause adherence of sodium carbonate, crystal deposition, clogging, or the like to occur in a tray/packed bed/dispersion apparatus/liquid collector or the like in the distillation equipment.

It is preferable to introduce an initial amount of a liquid containing dimethyl sulfoxide into a distillation system and then continuously supply the liquid containing dimethyl sulfoxide to the distillation equipment.

It is preferable to set the pressure during distillation in a range of atmospheric pressure to vacuum pressure. In particular, when a difference in the boiling point between dimethyl sulfoxide and impurities to be removed is small, impurities can be readily removed by increasing the difference in the boiling point between dimethyl sulfoxide and the impurities without decreasing the degree of vacuum to a significant extent.

As dimethyl sulfoxide is not decomposed even at high temperatures, a higher vacuum compared to conventional technology is not required. The temperature at the bottom of the distillation equipment is preferably 90° C. to 180° C. When the temperature at the bottom of the distillation equipment is 90° C. to 180° C., the range of distillation operation temperatures increases. This allows reduction of load on a vacuum apparatus at the overhead, a condenser, or a refrigerator, which is industrially preferable as an efficient and economical distillation purification method.

It is preferable to conduct distillation in an inert gas atmosphere and more preferable to conduct distillation in a nitrogen or argon atmosphere upon distillation at atmospheric pressure.

It is preferable to conduct continuous dehydration distillation to obtain dimethyl sulfoxide.

Sodium carbonate is mixed with a liquid containing dimethyl sulfoxide at the bottom of the distillation equipment and the portion is heated, thereby obtaining a distillate containing dimethyl sulfoxide at a position lower than a position at which the liquid containing dimethyl sulfoxide is initially introduced and higher than a position of the heating portion.

Preferably, a distillate rich in dimethyl sulfoxide compared to a feed material supplied to the distillation equipment is obtained at the position lower than the position at which the liquid containing dimethyl sulfoxide is introduced and higher than the position of the heating portion.

The distillation equipment is preferably a single multistage distillation tower.

Preferably, low-boiling point components containing water are drawn off from the overhead, high-boiling point components are discharged from the tower bottom, and a distillate rich in dimethyl sulfoxide is discharged from the side cut below a stage for supplying a distillation feed material.

Preferably, vapor or liquid present in the distillation equipment is utilized as a heating medium of other equipments.

Preferably, simultaneous continuous distillation separation of lightends (low-boiling point components) containing water and heavyends (high-boiling point components) is carried out by a single distillation equipment.

Dimethyl sulfoxide obtained by the method of distilling dimethyl sulfoxide contains fewer impurities and has high purity. Dimethyl sulfoxide obtained by the method of distilling dimethyl sulfoxide can be used as a liquid to remove photoresists as electronic materials, a liquid for synthesis of medicines and pesticides, a liquid to remove/wash lend molds or the like, a solvent used in a step of polymerization of polymers such as cellulose, polyimide, polysulfone, polyurethane, and polyacrylonitrile or spinning of fibers of such polymers, or a liquid for removing paints.

The multistage distillation tower is a multistage distillation tower for distilling a liquid containing dimethyl sulfoxide.

The multistage distillation tower includes preferably a distillation tower for concentration purification via a vapor-liquid contact, a condenser that condenses vapor of lightends containing water to obtain a condensation liquid, and a reboiler that generates dimethyl sulfoxide vapor by evaporating the liquid by heating.

The multistage distillation tower includes an apparatus that adds sodium carbonate at the tower bottom of the distillation tower. Preferably, to allow sodium carbonate to be present at a concentration within a certain range, sodium carbonate is continuously or intermittently supplied at the tower bottom portion in the multistage distillation tower. Preferably, the multistage distillation tower has an apparatus that directly adds sodium carbonate at the bottom of the distillation tower. Sodium carbonate may be supplied in the crystal solid itself or in the solution or suspension/slurry mixed with dimethyl sulfoxide from an apparatus that directly adds sodium carbonate.

Preferably, lightends containing water are drawn off from the overhead, heavyends are drawn off from the tower bottom, and a distillate rich in dimethyl sulfoxide is discharged from the side cut below a stage that supplies a distillation feed material in the multistage distillation tower.

More preferably, the multistage distillation tower is prepared as a single tower in a manner such that lightends containing water are drawn off from the overhead, heavyends are drawn off from the tower bottom, and a distillate rich in dimethyl sulfoxide is drawn off from the side cut below a stage that supplies a distillation starting material. More preferably, the multistage distillation tower separates lightends containing water and heavyends by simultaneous continuous distillation with a single distillation equipment.

The number of stages of the distillation tower to achieve a vapor-liquid contact is preferably 2 to 50 stages and more preferably 3 to 40 stages.

In one example, the multistage distillation tower might be a tray-type or packing bed-type. To reduce heat deterioration of dimethyl sulfoxide, a packing bed-type is preferable, and a regular structure packing bed-type is more preferable because the duration of flux/retention in the tower can be shortened and the operation is stabilized.

The multistage distillation tower is provided with a system capable of mixing sodium carbonate with a liquid containing dimethyl sulfoxide at a tower bottom of the distillation tower while controlling the concentration of sodium carbonate to 0.005% to 25% by weight relative to 100% by weight of the liquid containing dimethyl sulfoxide and sodium carbonate in total at a tower bottom of the distillation tower and heating the bottom.

The multistage distillation tower has a side cut that allows a distillate containing dimethyl sulfoxide to flow out at a position lower than a position of a supply stage that supplies a liquid containing dimethyl sulfoxide and higher than a position of the heated portion.

Either a liquid or vapor may be drawn off as a distillate containing dimethyl sulfoxide form the side cut. A product in the required form is obtained at a required temperature via a condenser for a distillate containing dimethyl sulfoxide in the vapor or via a cooler for a distillate containing dimethyl sulfoxide in the liquid.

Preferably, the multistage distillation tower is provided with a stage that purifies dimethyl sulfoxide at least one of an upper portion and a lower portion of the side cut that allows a distillate containing dimethyl sulfoxide to be drawn off.

The multistage distillation tower may employ either a tray-type or a packing bed-type for a concentration portion and a recovery portion of the distillation tower, and either random packings or structure packings may be used for a packing bed.

A liquid distributer, a liquid collector, and a packed bed support are provided in the distillation tower, if necessary. In the explanatory drawings, a kettle-type reboiler is directly installed to the bottom portion of the distillation tower in one example Meanwhile, an alternative system may have a structure in which a distillation tower and a reboiler connected via a pipe, are independently provided and a liquid or vapor is transferred therebetween via thermosiphon or pump circulation or the like.

The temperature of the bottom portion of the distillation tower is preferably 90° C. to 180° C. Further, to make attempts to recover and efficiently use sensible heat/evaporative latent heat of the in-process liquid/vapor for energy saving, it is preferable to conduct continuous distillation while the temperature of the bottom portion of the distillation tower is 150° C. to 180° C.

Preferably, the multistage distillation tower is provided with a pipe by which vapor condensed in a condenser installed at the overhead of the distillation tower, a pipe by which condensed liquid is partially refluxed back to the distillation tower and a pipe by which the condensed liquid is partially drawn off as a waste liquid. Preferably, the multistage distillation tower has a structure in which a vent pipe of the condenser connects to a vacuum generator such as a vacuum pump or ejector.

Preferably, the multistage distillation tower includes a condenser for overhead vapor, and the condenser for overhead vapor also functions as a heater, boiler, or reboiler for a different fluid in other equipments.

The multistage distillation tower functions to suppress decomposition of dimethyl sulfoxide without forced circulation/stirring liquid at the tower bottom.

Scaling of decomposition inhibitors, crystal deposition, and clogging do not occur in a tray/packing bed/liquid distributer/liquid collector or the like of the distillation tower, thereby allowing stable operation for many hours.

Dimethyl sulfoxide obtained by using the multistage distillation tower contains fewer impurities and has high purity. Dimethyl sulfoxide obtained by using the multistage distillation tower can be used as a liquid to remove photoresists as electronic materials, a liquid for synthesis of medicines and pesticides, a liquid to remove washing lend molds or the like, a solvent used in a step of polymerization of polymers such as cellulose, polyimide, polysulfone, polyurethane, and polyacrylonitrile or spinning of fibers of such polymers, or a liquid to remove paints.

Figure 1:
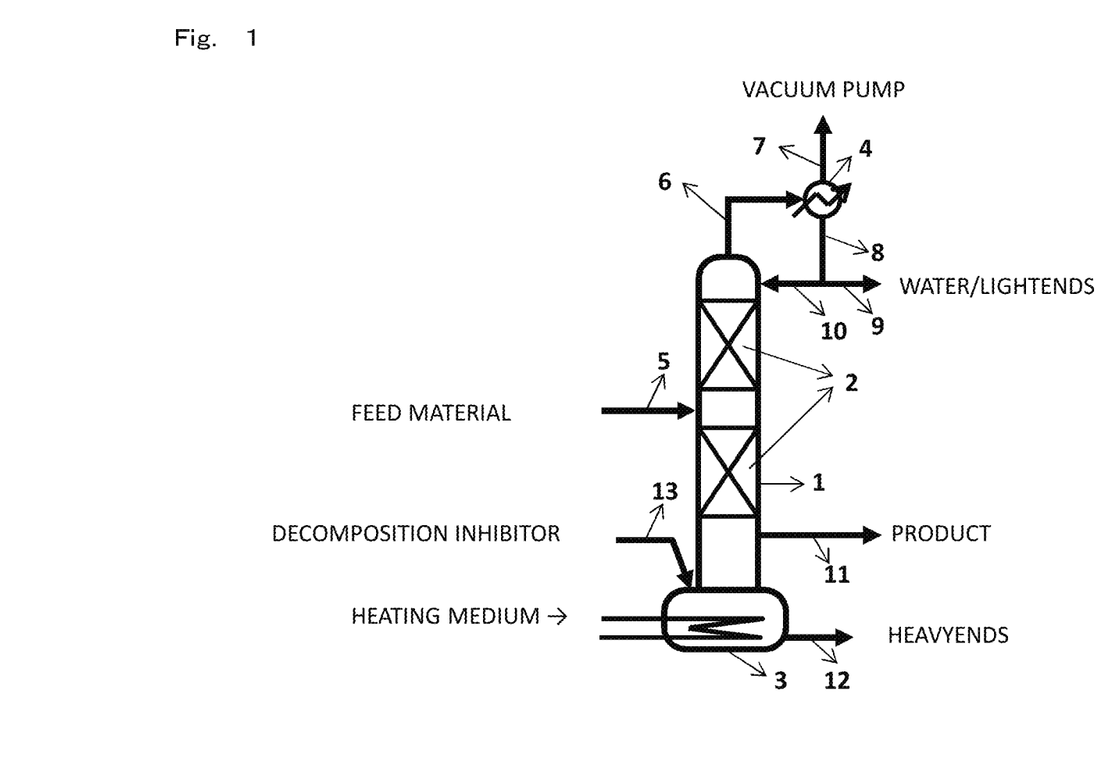
FIG. 1 illustrates an example of a distillation equipment used for the method of distilling dimethyl sulfoxide, which is the multistage distillation tower.

FIG. 1 illustrates an example of a distillation equipment used for the method of distilling dimethyl sulfoxide. The distillation equipment illustrated in FIG. 1 is also an example of the multistage distillation tower.

Figure 7:
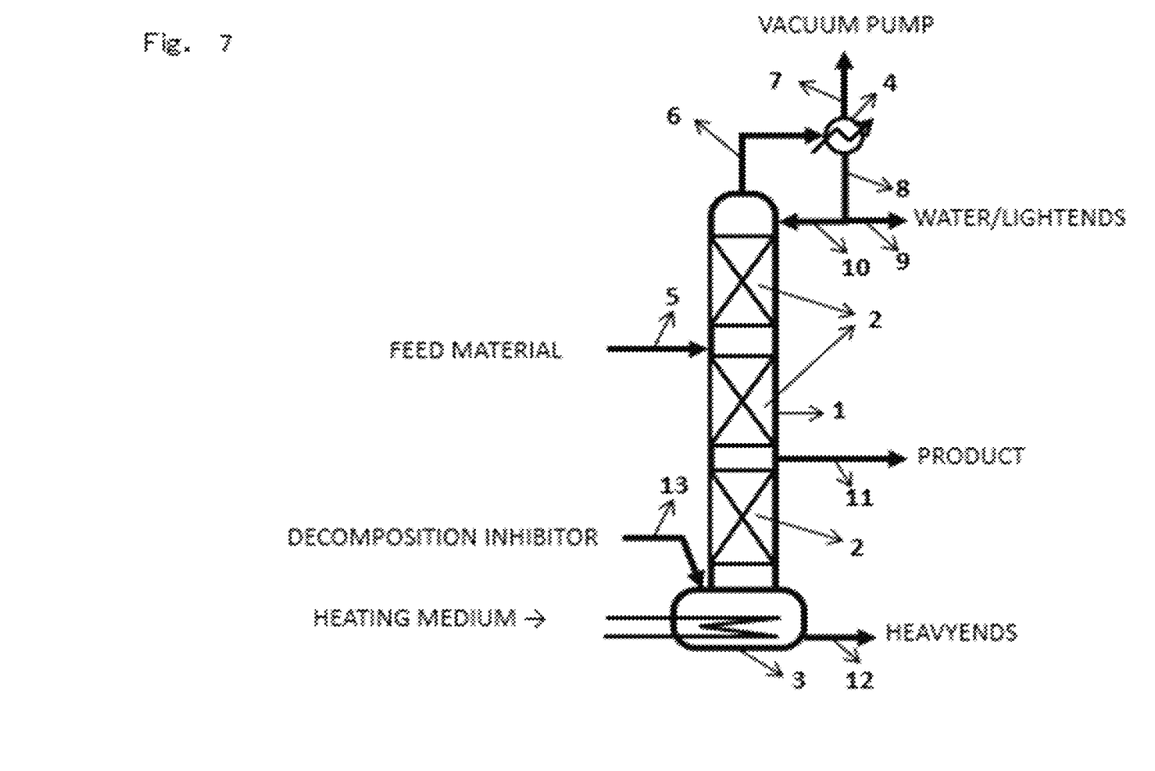
FIG. 7 illustrates an example of a distillation system used for the method of distilling dimethyl sulfoxide, which is the multistage distillation tower. A purification stage is provided below the side cut to draw off a product.

In the multistage distillation tower illustrated in FIG. 1, lightends (low-boiling point components) containing water are drawn off from the overhead, heavyends (high-boiling point components) are drawn off from the tower bottom, and a liquid containing dimethyl sulfoxide is supplied via a pipe that supplies a feed material for distillation (5) in FIG. 1 before distillation. Sodium carbonate serving as a decomposition inhibitor is introduced via a pipe that adds a decomposition inhibitor (sodium carbonate) (13) to the bottom portion of the distillation tower, at which a reboiler is connected to the distillation tower. Dimethyl sulfoxide heated by a reboiler (3) in FIG. 1 is purified and drawn off from a pipe that draws off a dimethyl sulfoxide product via a side cut (11) in FIG. 1. The pipe that draws off a dimethyl sulfoxide product via a side cut is installed at a position lower than the position of the pipe that supplies a feed material for distillation. For the purpose of promoting purification/removal of heavyends, a distillation tower, in which a purification stage is provided below the side cut that draws off a product as shown in FIG. 7, is preferably employed.

Figure 8:
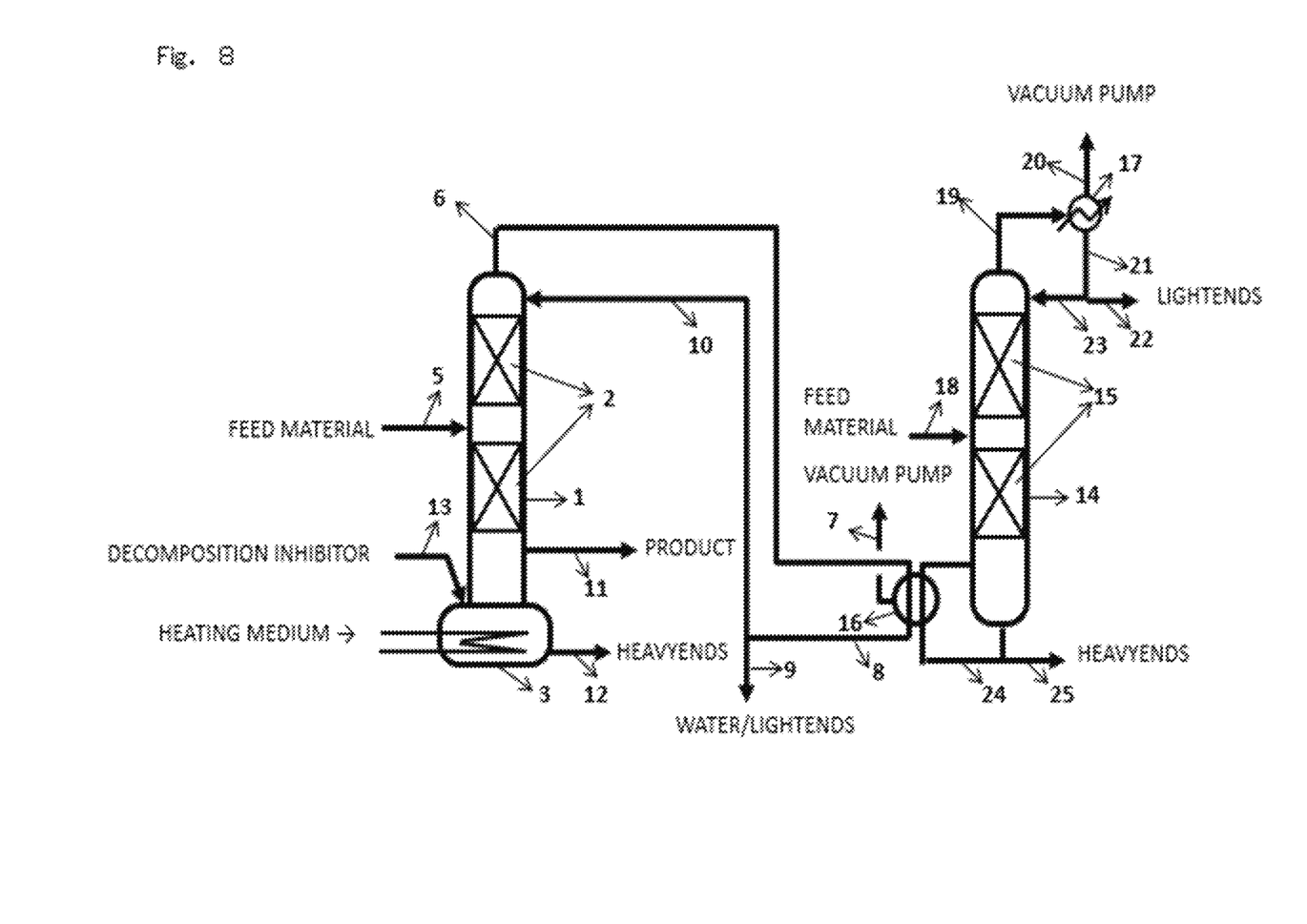
FIG. 8 illustrates an example of a distillation system used for the method of distilling dimethyl sulfoxide, which is the multistage distillation tower. A different distillation tower is installed in the multistage distillation tower.

FIG. 8 illustrates an example of the distillation system in which evaporative latent heat of vapor at the overhead is recovered and effectively used for energy saving. The distillation system illustrated in FIG. 8 is also an example of the multistage distillation tower. The multistage distillation tower is intended to conduct heat exchange between the bottom liquid of other distillation tower and the overhead vapor of the multistage distillation tower, thereby reducing heating energy of other distillation tower. The dimethyl sulfoxide distillation temperature corresponding to the overhead vapor temperature can be increased, thereby making it possible to extend the application of energy saving through exhausted heat recovery.

EXAMPLES

Hereinafter, our methods and systems will be specifically described with reference to the Examples.

In this Example, the gas chromatographic purity (area %) of dimethyl sulfoxide was determined by gas chromatography under the following conditions.

Apparatus used: Shimadzu Corporation GC-2010 (FID)
Column: DB-WAX 0.25 mm×60 m, film thickness of 0.25 μm
Carrier gas: He 165.7 kPa
Column temperature increase conditions: 35° C.→7° C./minute→140° C. 10 minutes→15° C./minute→250° C. 10 minutes
Inlet temperature: 200° C.
Detector temperature: 250° C.
FID Air: 400 ml/min
  H2: 40 ml/min
  Make-up: 30 ml/min
Split ratio: 14
Preparation of analysis sample: A sample was filtered through a 0.5 μm PTFE, syringe filter.
Injection volume: 1.0 μl.

Reference Example 1

Aqueous dimethyl sulfoxide (moisture content measured by a Karl Fischer moisture titrator: 33.3% by weight; dimethyl sulfoxide: 66.7% by weight) in an amount of 200 g and sodium carbonate serving as an additive in an amount accounting for an initial concentration of 0.02% by weight were added to a 1 L four-necked flask equipped with a Dimroth condenser, a receiver for a distillate, a stirrer, and a thermometer necessary for a simple distillation technique. The calculation formula of the initial concentration is:

Initial concentration (%)=[Amount of sodium carbonate to be added (g)]/[Initial weight of aqueous dimethyl sulfoxide (g)+Amount of sodium carbonate to be added (g)]×100

The inner part of the flask was substituted by nitrogen, and then, a rubber balloon filled with nitrogen was attached to an upper portion of the Dimroth condenser so that the flask was hermetically sealed. The flask was heated in an oil bath at 192° C. After 80 g of a distillate containing water was distilled, the flask was further heated such that the internal temperature reached 180° C. Subsequently, the flask was heated at 180±2° C. for 24 hours. The amount of sodium carbonate in the liquid in the flask during heating at 180±2° C. for 24 hours decreased by 80 g as compared with the initial concentration upon introduction of starting materials as shown in Table 1. Therefore, the sodium carbonate concentration was 1.67 times the initial concentration (=200 g/(200 g−80 g)).

After cooling to 25° C. or less, the liquid adhering to the walls inside of the flask and the internal liquid of the flask were mixed. The gas chromatographic purity (area %) of dimethyl sulfoxide of the heated internal liquid was determined:

Decomposition rate=[Gas chromatographic purity (%) of unheated dimethyl sulfoxide−Gas chromatographic purity (%) of heated dimethyl sulfoxide]/Gas chromatographic purity (%) of unheated dimethyl sulfoxide×100.

Table 1 lists the results of the decomposition rate (area %/hr) of dimethyl sulfoxide calculated in accordance with the above.

Reference Examples 2 to 6

Reference Examples 2 to 6 were carried out as with Reference Example 1 except that the sodium carbonate concentration was changed as shown in Table 1. Table 1 shows the results.

Reference Example 7

Reference Example 7 was carried out as with Reference Example 1 except that sodium carbonate was not added. Table 1 shows the results.

Reference Example 8

Reference Example 8 was carried out as with Reference Example 1 except that sodium carbonate was not added as an additive, and sodium hydroxide was added at an initial concentration of 0.01% by weight (the calculation formula of the initial concentration is:

Initial concentration (%)=[Amount of sodium hydroxide to be added (g)]/[Initial weight of aqueous dimethyl sulfoxide (g)+Amount of sodium hydroxide to be added (g)]×100.

Table 2 shows the results of the amount of sodium hydroxide in the liquid in the flask during heating at 180±2° C. for 24 hours decreased by 80 g compared to the initial concentration upon introduction of feed materials as shown in Table 2. Therefore, the sodium carbonate concentration was 1.67 times the initial concentration (=200 g/(200 g−80 g)).

After cooling to 25° C. or less, the liquid adhering to the walls inside of the flask and the internal liquid of the flask were mixed as with Reference Example 1. The gas chromatographic purity (area %) of dimethyl sulfoxide of the heated internal liquid was determined:

Decomposition rate=[Gas chromatographic purity (%) of unheated dimethyl sulfoxide−Gas chromatographic purity (%) of heated dimethyl sulfoxide]/Gas chromatographic purity (%) of unheated dimethyl sulfoxide×100.

Table 2 lists the results of the decomposition rate (area %/hr) of dimethyl sulfoxide calculated in accordance with the above.

Reference Examples 9 and 10

Reference Examples 9 and 10 were carried out as with Reference Example 8 except that the sodium hydroxide concentration was changed as shown in Table 2. Table 2 shows the results.

It is understood from Reference Examples 1 to 10 that sodium carbonate can stably exhibit the effect of inhibiting decomposition of dimethyl sulfoxide in a significantly wider concentration range compared to sodium hydroxide that is conventionally known as a decomposition inhibitor even at high temperatures close to the boiling point under atmospheric pressure.

TABLE 1

|  | Reference Example 1 | Reference Example 2 | Reference Example 3 | Reference Example 4 | Reference Example 5 | Reference Example 6 | Reference Example 7 |
|---|---|---|---|---|---|---|---|
| Initial concentration of sodium carbonate (wt %) | 0.02 | 0.05 | 0.06 | 0.09 | 0.60 | 15 | Not added |
| Concentration of sodium carbonate in liquid in the flask heated and maintained at 180 ± 2° C. for 24 hours (wt %) | 0.03 | 0.08 | 0.10 | 0.15 | 1.00 | 25 | 0 |
| Dimethyl sulfoxide decomposition rate (area %/hr) | 0.001 | 0.001 | 0.001 | 0.001 | 0.001 | 0.001 | 0.068 |

TABLE 2

|  | Reference Example 8 | Reference Example 9 | Reference Example 10 |
|---|---|---|---|
| Initial concentration of sodium hydroxide (wt %) | 0.01 | 0.06 | 0.60 |
| Concentration of sodium carbonate in liquid in the flask heated and maintained at 180 ± 2° C. for 24 hours (wt %) | 0.02 | 0.10 | 1.00 |
| Dimethyl sulfoxide decomposition rate (area %/hr) | 0.003 | 0.007 | 0.795 |

Example 1

Continuous dehydration distillation purification of aqueous dimethyl sulfoxide at 33% by weight was carried out using a continuous distillation system (distillation tower: having a tower diameter of 65 mm and containing structure packings for 5 stages at a concentration zone above a portion that supplies feed materials and at a recovery portion below the same) illustrated in FIG. 1. Example 1 will be explained with reference to the drawings.

Figure 2:
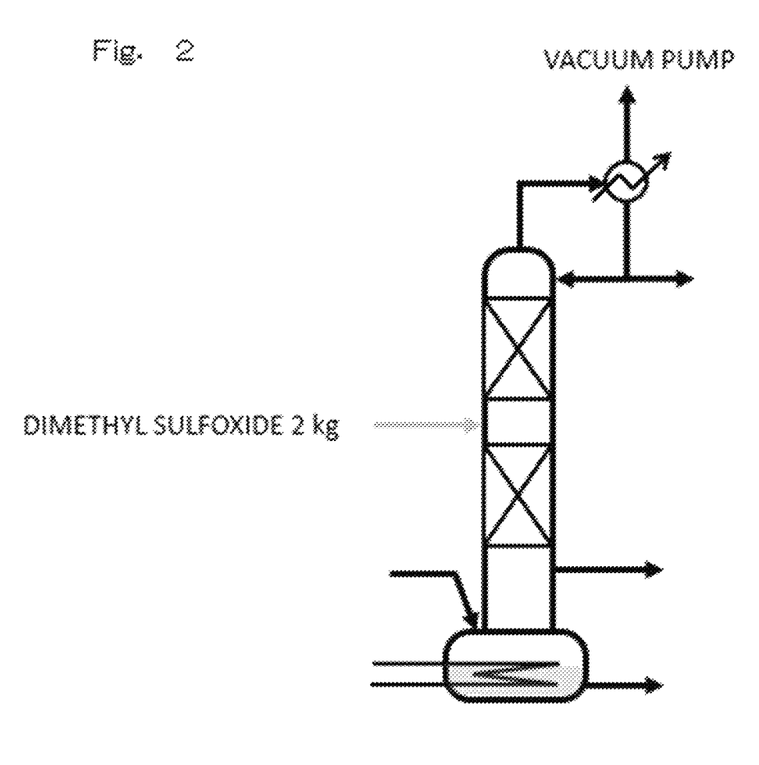
FIG. 2 explains the distillation purification of dimethyl sulfoxide in Example 1. Dimethyl sulfoxide was preliminarily introduced in an amount of 2 kg into a bottom of the distillation tower provided with a reboiler prior to the start of heating.
Figure 3:
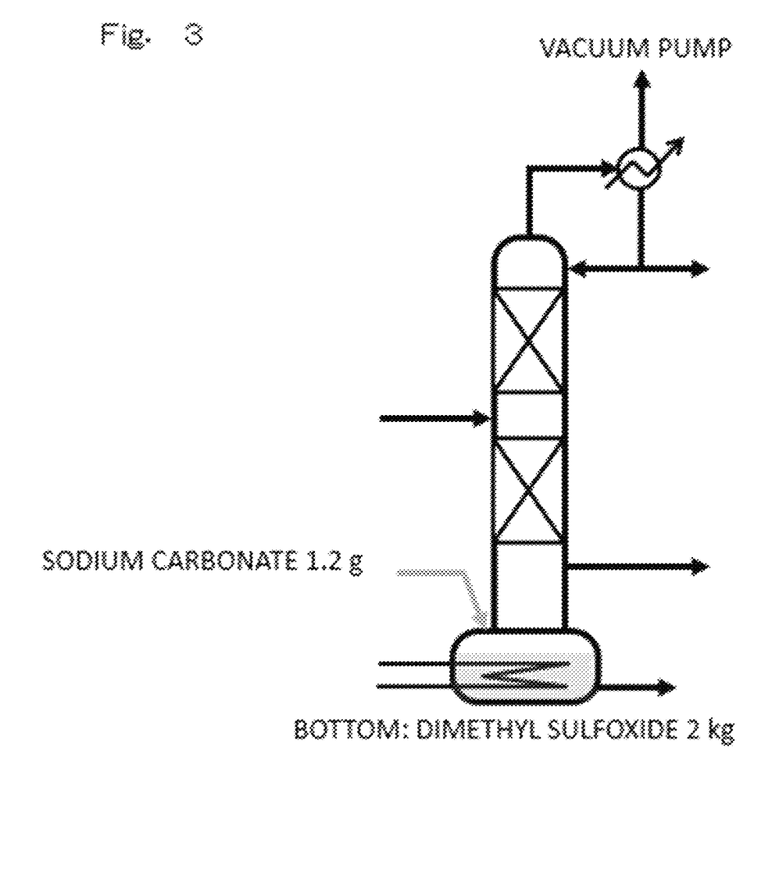
FIG. 3 explains the distillation purification of dimethyl sulfoxide in Example 1. Sodium carbonate was added at the bottom of the distillation tower.
Figure 4:
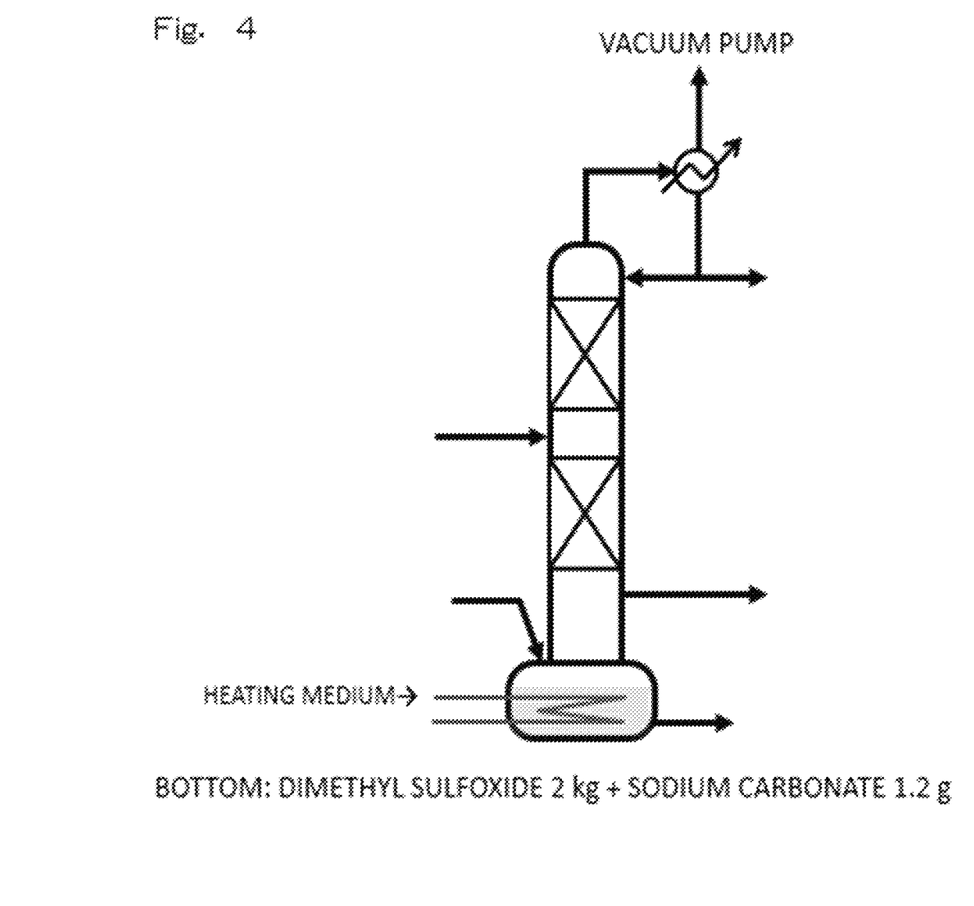
FIG. 4 explains the distillation purification of dimethyl sulfoxide in Example 1. Dimethyl sulfoxide and sodium carbonate are present at the bottom of the distillation tower.
Figure 5:
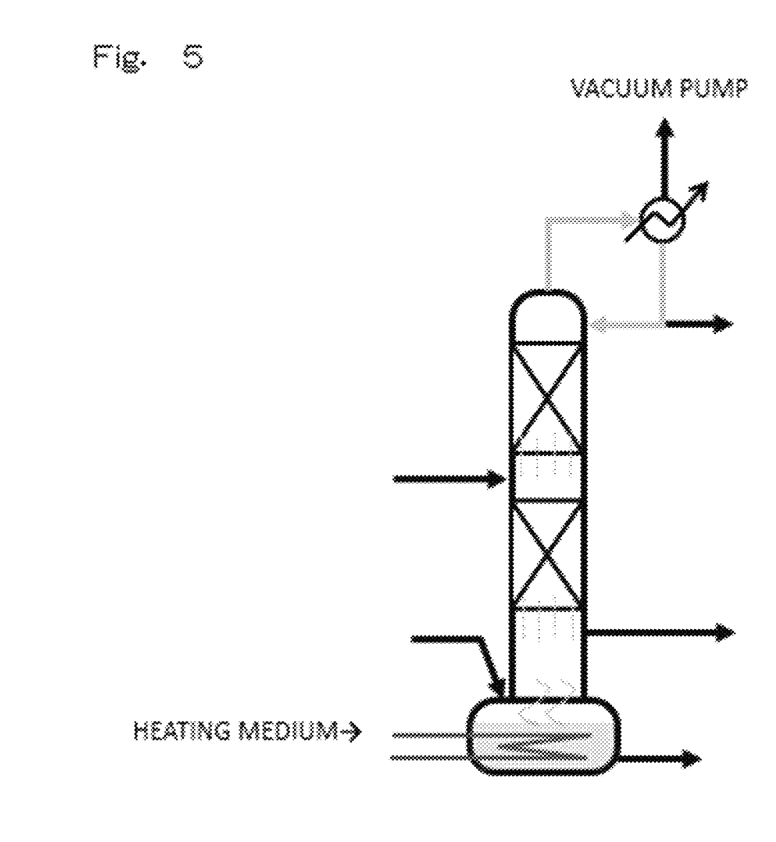
FIG. 5 explains the distillation purification of dimethyl sulfoxide in Example 1. After the start of heating, distillation started from the overhead and then the distillation status was stabilized by total reflux.

Dimethyl sulfoxide was preliminarily introduced in an amount of 2 kg into a bottom portion of the distillation tower provided with a reboiler prior to the start of heating (FIG. 2). Sodium carbonate in an amount of 1.2 g was added thereto (FIG. 3). The sodium carbonate concentration at a bottom of the distillation tower was calculated based on the initial amounts of dimethyl sulfoxide and sodium carbonate (1.2 g/(2000 g+1.2 g) and determined to be 0.06% by weight (FIG. 4). Thereafter, the distillation tower was vacuumed, heating was started for boiling, and total reflux was carried out after the start of distillation from the overhead for 30 minutes for stabilization (FIG. 5).

Figure 6:
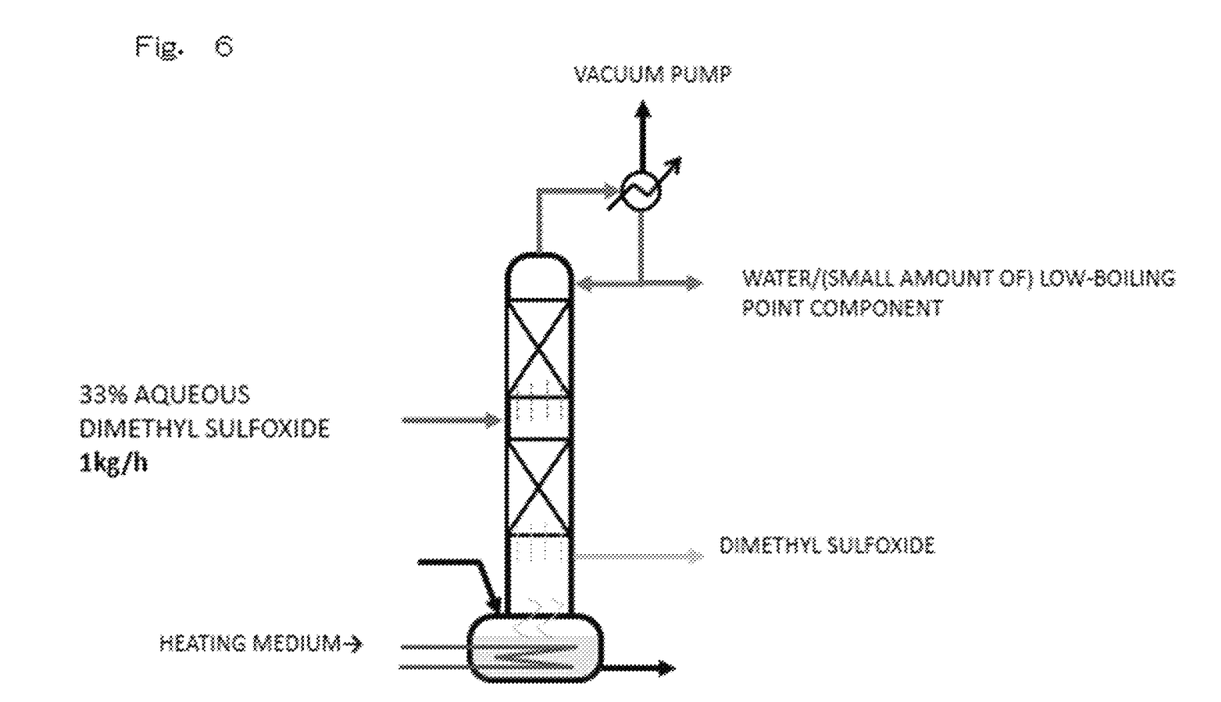
FIG. 6 explains the distillation purification of dimethyl sulfoxide in Example 1. A liquid concentrate of aqueous dimethyl sulfoxide was supplied from a middle stage of the distillation tower, and a dimethyl sulfoxide product in the liquid form was drawn off via a side cut thereof, followed by continuous dehydration distillation.

Next, an aqueous dimethyl sulfoxide liquid concentrate at 33% by weight was continuously supplied from the middle stage of the distillation tower at a rate of 1 kg/h, low-boiling point components containing water were drawn off from the overhead and a dimethyl sulfoxide product in the liquid phase was drawn off via a side cut formed immediately below the recovery portion, and continuous dehydration distillation was started (FIG. 6). The amount of a product discharged from the overhead and the amount of a product discharged via the side cut were adjusted such that the yield of dimethyl sulfoxide obtained as a product was set to 94% (based on the net amount of dimethyl sulfoxide in the liquid concentrate). A product at the tower bottom portion was held and not discharged. The reflux ratio was set to 3.0, and the distillation pressure was adjusted such that the tower bottom temperature was set to 108° C.

Table 3 shows the impurity concentration in dimethyl sulfoxide contained in the liquid feed, the impurity concentration in dimethyl sulfoxide obtained as a product, the moisture content of dimethyl sulfoxide obtained as a product, and the yield of dimethyl sulfoxide obtained as a product. The moisture content was determined using a Karl Fischer moisture titrator.

Example 2

Example 2 was carried out as with Example 1 except that the distillation pressure was adjusted such that the tower bottom temperature was set to 108° C. Table 3 shows the results.

Example 3

Example 3 was carried out as with Example 2 except that structure packings for 5 stages were installed under the side cut that draws off a dimethyl sulfoxide product for the purpose of promoting purification of the product/removal of high-boiling point components. Table 3 shows the results.

Comparative Example 1

Comparative Example 1 was carried out as with Example 1 except that the distillation pressure was adjusted such that no additive was added to the tower bottom portion and the tower bottom temperature was set to 94° C. Table 3 shows the results.

TABLE 3

| | Concentration of Sodium carbonate in tower bottom liquid | Tower bottom temperature | Impurity concentration (area ppm) | | | | Moisture | Dimethyl sulfoxide yield |
|---|---|---|---|---|---|---|---|---|
| | | | DMS | EMSO | DMSO2 | TMM | | |
| Example 1 | 0.06% | 95° C. | Not detected | 6 | 2 | Not detected | 0.03% | 94% |
| Example 2 | 0.06% | 108° C. | 0 | 7 | 2 | Not detected | 0.03% | 94% |
| Example 3 | 0.06% | 108° C. | 0 | 4 | 1 | Not detected | 0.03% | 94% |
| Comparative Example 1 | Not added | 94° C. | 4 | 11 | 14 | 1 | 0.03% | 94% |
| (Impurities in dimethyl sulfoxide starting material free of water) | — | — | 5 | 8 | 8 | 2 | — | — |

DMS: Dimethyl sulfoxide
EMSO: Ethyl methyl sulfoxide
DMSO2: Dimethyl sulfone
TMM: Tris(methylthio)methane By allowing sodium carbonate to be present as a decomposition inhibitor at the tower bottom of the distillation tower, it was possible to obtain dimethyl sulfoxide containing fewer impurities by stable continuous distillation. It was possible to conduct continuous distillation under high temperature conditions at from 95° C. to 108° C. In addition, when continuous distillation was conducted with the addition of a purification stage below the side cut at 108° C. as in the above case, it was possible to stably remove ethyl methyl sulfoxide and dimethyl sulfone as high-boiling point components.

INDUSTRIAL APPLICABILITY

According to our method of distilling dimethyl sulfoxide, a compact system is achieved and, thus, the system construction investment cost is low. Further, as the temperatures of an in-process liquid and vapor in a distillation tower increase, it is possible to reduce the amount of energy used in the system as a whole by reusing energy through recovery of sensible heat and latent heat of the in-process liquid and vapor. This allows distillation purification of dimethyl sulfoxide at a low purification cost in an economical manner.

Dimethyl sulfoxide obtained by our method of distilling dimethyl sulfoxide contains fewer impurities and has high purity. Dimethyl sulfoxide obtained by our method of distilling dimethyl sulfoxide can be used as a liquid to remove photoresists as electronic materials, a liquid for synthesis of medicines and pesticides, a liquid to remove/wash lend molds or the like, a solvent used in a step of polymerization of polymers such as cellulose, polyimide, polysulfone, polyurethane, and polyacrylonitrile or spinning of fibers of such polymers, or a liquid to remove paints.

According to our multistage distillation tower, as the temperatures of an in-process liquid and vapor in a distillation tower increase, it is possible to reduce the amount of energy used in the system as a whole by reusing energy through recovery of sensible heat and latent heat of the in-process liquid and vapor. This allows distillation purification of dimethyl sulfoxide at a low purification cost in an economical manner.

Dimethyl sulfoxide recovered or purified according to the multistage distillation tower contain fewer impurities and has high purity. Dimethyl sulfoxide according to our method of distilling dimethyl sulfoxide can be widely used as a solvent for removal or washing of electronic materials, synthesis of medicines and pesticides, polymer polymerization, spinning of fibers of such polymers and the like.

The invention claimed is:

1. A method of distilling a liquid containing dimethyl sulfoxide using a single multistage distillation tower, comprising:
   (1) contacting sodium carbonate and a liquid containing dimethyl sulfoxide at a bottom portion of the distillation system such that sodium carbonate accounts for 0.005% to 25% by weight relative to 100% by weight of the liquid containing dimethyl sulfoxide and sodium carbonate in total at the bottom portion of the single multistage distillation tower and heating the bottom portion with a heater, wherein sodium carbonate is directly added at the bottom Portion of the single multistate distillation tower; and
   (2) obtaining a distillate containing dimethyl sulfoxide at a position lower than a position at which the liquid containing dimethyl sulfoxide is introduced and higher than a position of the heater.

2. The method according to claim 1, wherein a distillate rich in dimethyl sulfoxide compared to a feed material supplied to the single multistate distillation tower is obtained at the position lower than the position at which the liquid containing dimethyl sulfoxide is initially introduced and higher than the position of the heater.

3. The method according to claim 1, wherein the temperature of the bottom portion of the single multistate distillation tower is 90° C. to 180° C.

4. The method according to claim 1, wherein after the liquid containing dimethyl sulfoxide is introduced into the single multistate distillation tower, the liquid containing dimethyl sulfoxide is continuously supplied to the distillation system.

5. The method according to claim 1, wherein the distillate containing dimethyl sulfoxide is obtained by continuous dehydration distillation.

6. The method according to claim 1, wherein vapor generated or liquid contained in the single multistate distillation tower is utilized as a heat medium.

7. The method according to claim 1, wherein simultaneous continuous distillation separation of low-boiling point components containing water and high-boiling point components having higher boiling points compared to the low-boiling point components is carried out by the single multistate distillation tower.

8. A multistage distillation tower that distills a liquid containing dimethyl sulfoxide, which is a single multistate distillation tower, comprising:
   an apparatus that directly adds sodium carbonate at the bottom portion of the single multistate distillation tower, and
   a system that contacts the sodium carbonate with a liquid containing dimethyl sulfoxide at the bottom portion of the distillation tower and heats the bottom portion with a heater, while controlling the concentration of sodium carbonate to 0.005% to 25% by weight relative to 100% by weight of the liquid containing dimethyl sulfoxide and sodium carbonate in total at the bottom portion of the single multistate distillation tower, and
   a side cut that allows a distillate containing dimethyl sulfoxide to flow out at a position lower than a position of a supply stage that supplies a liquid containing dimethyl sulfoxide and higher than a position of the heater.

9. The multistage distillation tower according to claim 8, wherein low-boiling point components containing water are discharged from an overhead of the tower, high-boiling point components are drawn off from the tower bottom, and a distillate rich in dimethyl sulfoxide is drawn off from the side cut below a stage that supplies a distillation feed material.

10. The multistage distillation tower according to claim 8, wherein the temperature of the bottom portion of the distillation tower temperature is 90° C. to 180° C.

11. The multistage distillation tower according to claim 8, wherein the apparatus that adds sodium carbonate at the bottom portion of the distillation tower directly adds the sodium carbonate.

12. The multistage distillation tower according to claim 8, further comprising a stage that purifies dimethyl sulfoxide at at least one of an upper portion and a lower portion of the side cut that allows the distillate containing dimethyl sulfoxide to be drawn off.

13. The multistage distillation tower according to claim 8, further comprises an overhead vapor condenser that functions as a heater, boiler, or reboiler for a different fluid.

\* \* \* \* \*